(12) United States Patent
Tamer

(10) Patent No.: US 12,105,611 B2
(45) Date of Patent: Oct. 1, 2024

(54) ACTIVITY TRACKING SYSTEM

(71) Applicant: Ayse Selin Tamer, Istanbul (TR)

(72) Inventor: Ayse Selin Tamer, Istanbul (TR)

(*) Notice: Subject to any disclaimer, the term of this patent is extended or adjusted under 35 U.S.C. 154(b) by 538 days.

(21) Appl. No.: 17/429,369

(22) PCT Filed: Apr. 1, 2021

(86) PCT No.: PCT/TR2021/050297
§ 371 (c)(1),
(2) Date: Aug. 9, 2021

(87) PCT Pub. No.: WO2022/211749
PCT Pub. Date: Oct. 6, 2022

(65) Prior Publication Data
US 2022/0318123 A1      Oct. 6, 2022

(30) Foreign Application Priority Data
Mar. 31, 2021   (TR) ................ 2021/005808

(51) Int. Cl.
*G06F 11/34* (2006.01)
*G06F 3/04847* (2022.01)
*G06F 17/40* (2006.01)

(52) U.S. Cl.
CPC ...... *G06F 11/3438* (2013.01); *G06F 3/04847* (2013.01); *G06F 17/40* (2013.01)

(58) Field of Classification Search
CPC .............. G06F 11/3438; G06F 1/1671; G06F 3/04847; G06F 1/163; G06F 17/40; G04F 10/00; G16H 40/67; G16H 20/10; G16H 20/30
See application file for complete search history.

(56) References Cited

U.S. PATENT DOCUMENTS

| | | | |
|---|---|---|---|
| 5,691,932 A | 11/1997 | Reiner et al. | |
| 7,522,477 B1 | 4/2009 | Sheldon | |
| 9,329,053 B2* | 5/2016 | Lakovic | G04G 17/045 |
| 11,175,635 B2* | 11/2021 | Wang | G06F 1/163 |
| 2008/0090216 A1 | 4/2008 | Clair | |
| 2008/0167535 A1 | 7/2008 | Stivoric et al. | |
| 2015/0121261 A1* | 4/2015 | Collado | G06F 3/04842 715/764 |
| 2020/0326663 A1 | 10/2020 | Wang et al. | |

FOREIGN PATENT DOCUMENTS

WO          2010126821 A1      11/2010

* cited by examiner

*Primary Examiner* — An H Do
(74) *Attorney, Agent, or Firm* — Bayramoglu Law Offices LLC

(57) ABSTRACT

An activity tracking system has a plurality of activity tracking devices, each with a processor unit to receive an input signal associated with the activity, and a memory unit to keep record of at least one log associated with the activity via the processor unit. Herein, the activity tracking device comprises at least one input unit configured to be detachably attached onto the device body, and at least one input terminal associated with the processor unit within the device body to enable the input signal to be transmitted to the processor unit; and the input unit comprises at least one input means for the user to interact with the tracking device to generate an input signal, an inlet connector that is detachably attached to the input terminal to enable the input signal to be transmitted to the processor unit, and an identifier circuit for detecting the type of input unit.

23 Claims, 6 Drawing Sheets

FIG. 8A
FIG. 8C
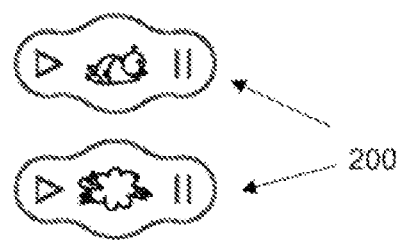
FIG. 8B

ACTIVITY TRACKING SYSTEM

CROSS REFERENCE TO THE RELATED APPLICATIONS

This application is the national phase entry of International Application No. PCT/TR2021/050297, filed on Apr. 1, 2021, which is based upon and claims priority to Turkish Patent Application No. 2021/005808, filed on Mar. 31, 2021, the entire contents of which are incorporated herein by reference.

TECHNICAL FIELD

The present disclosure relates to an activity tracking system consisting of an activity logging device with a processor unit to receive an input signal associated with the said activity, and a memory unit to keep record of at least one log associated with the said activity via the said processor unit, where the said log is dependent on the input signal.

BACKGROUND

There is a need to keep track of and log various activities with respect to the time at which the event happens and the duration/amount associated with that event as relevant. Example activities that can be logged include but are not limited to, breastfeeding, bottle feeding, bathing, playing games, measuring weight/height of babies; medicine intake, feeding, cleaning, resting, entertainment for elderly, patients and children; pumping milk for newborn mothers. Equipment maintenance in a company, plant watering in a locality, or feeding, medicine intake, walking for pets can also be listed as activities to be tracked.

Loggable activities can be categorized under three main types: logging the exact time of said activity, logging the exact time of said activity along with the duration of that activity and logging the exact time of said activity along with the amount related to that activity. Apart from manually taking notes, a variety of solutions exist in the present art to help users log activity data including the widely used mobile applications. However, none of the existing solutions are easy to use: mobile applications require the use of a mobile phone by the caregiver, who should launch the application and locate the correct activity and proceed with logging.

U.S. Pat. No. 7,522,477 relates to a single device that enables a plurality of events to be tracked. The described disclosure includes separate log buttons, separate timer buttons and separate screens for each of its predefined activities. Having a plurality of buttons, each button representing a single activity, located on a single user interface decreases the ease of use and can result in incorrect log entries. More importantly, since the predefined care activities are often performed in different locations, this solution requires the users to either move the device alongside or to travel to where the device is in order to log the activity.

The deficiencies of the state of art mentioned above necessitate an innovation to be proposed in the related technical field.

SUMMARY

The present invention relates to an activity tracking system, aiming to eliminate the disadvantages mentioned above and to introduce new advantages to the technical field in consideration.

The invention aims to introduce an activity tracking system that allows different activities to be tracked easily, conveniently and simultaneously.

Another aim of the invention is to introduce an activity tracking system in which data loss is reduced.

Another aim of the invention is to introduce an activity tracking system that allows sub-activities of the activities to be tracked.

Another aim of the invention is to introduce an activity tracking system that allows different types of activities to be tracked with an activity tracking device consisting of a reduced number of buttons as compared to the state of art solutions.

Another aim of the invention is to enable a device that is used to track a specific activity to be reused to track a different activity.

Another aim of the invention is to provide the time that activity was last performed to the user in a simple way.

Another aim of the invention is to provide remote access to the logged activities.

Another aim of the invention is to provide the ability to analyze and edit activity logs.

Another aim of the invention is to provide users with missed activity notifications for scheduled activities.

In order to fulfill all the aims mentioned above as well as the ones that emerge from the detailed description below, The present disclosure relates to an activity tracking system consisting of an activity logging device with a processor unit to receive an input signal associated with the said activity, and a memory unit to keep record of at least one log associated with the said activity via the said processor unit, where the said log is dependent on the input signal. In this respect, the innovation includes the tracking device to be composed of at least one input unit configured as attachable/detachable to its body; and at least one input terminal associated with the processor unit provided in the said body to enable the input signal to be transmitted to the processor unit;

an input unit consisting of at least one input means for the user to interact and generate an input signal during this interaction; an inlet connector that is detachably attached to the said input terminal to enable the input signal generated by the said input means to be transmitted to the said processor unit, and an identifier circuit that enables the said processor unit to determine the type of the attached input unit, when the said identifier circuit is linked to the said processor unit. The innovation also incorporates the said processor unit to be configured to detect the type of the input unit via the identifier circuit to which the said processor unit is linked and to evaluate the input signals received from the said input unit in accordance with the detected type. Therefore, in spite of having a reduced number of input means, the tracking device can be used to track different activities having different data entry requirements to be evaluated differently by the processor unit. Due to the said input unit being attachable/detachable, the input unit suitable for the activity to be tracked can be attached to the tracking device, and the activity can be logged through a single input means when required. This makes it easier for the users to track the activity and prevents them from logging in incorrectly. Additionally, since there exist different types of input units, one can select the input unit in accordance with the activity to be tracked so that it can comprise only of the input means to be used in the related activity. Therefore, eliminating the idle (non-used) input means from the tracking device increases the ease of use.

In a possible embodiment of the invention, said processor unit encapsulates at least one identifier terminal to detect the type of the said input unit that is attached to the tracking body; and it encapsulates at least one identification component, associated with the said identifier circuit which is attachable/detachable to the identifier terminal to enable the connection between the identifier circuit and the processor unit.

In another possible embodiment of the invention, said processor unit is configured to generate an activity record for an activity matching the detected type, when it receives an input signal.

In another embodiment of the invention, in the case of pluralities of input means; at least one of the input means is a primary input means and at least one of the other input means is a sub-input means. With such configuration, the processor unit performs the process steps matching the detected type when it receives an input signal from one of the sub-input means, and generates an activity record for the said activity with respect to the result of the said process steps when it receives an input signal from the primary input means.

In another possible embodiment of the invention, said process steps are at least one of the followings:
  incrementing the amount associated with the activity by a predetermined value,
  decrementing the amount associated with the activity by a predetermined value. In another possible embodiment of the invention, said process steps are as follows:
  recording the time when an input signal is received from one of the sub-input means as the first time,
  recording the time when an input signal is received from another sub-input means as the second time,
  determining the difference between the second time and the first time.

In yet another embodiment of the invention, said process steps are as follows:
  starting a stopwatch when an input signal is received from one of the sub-input means,
  stopping the stopwatch when an input signal is received from another sub-input means,
  determining the elapsed time.

The processor unit can determine the type of the attached input units, and the functionality of the input means on the input unit are adjusted by the processor unit to adapt the desired activity. This way, users can track/record different activities by simply attaching the appropriate input unit to the body of the tracking device.

In another possible embodiment of the invention, said tracking device consists of an input unit slot having a form compatible with the form of the input unit, for the placement of the input unit on the tracking device.

In another possible embodiment of the invention, said tracking device consists of a primary magnetic immobilization component and said input unit consists of a secondary magnetic immobilization component, where one of the primary and secondary magnetic immobilization components is a magnet and the other one is either a magnet or contains ferromagnetic material. This way, attaching the input unit to the tracking device is made simple and easy.

In another possible embodiment of the invention, said input unit consists of a selection switch operating in two different positions; and the processor unit is configured to perform the process steps and to record an activity in respect with the position of the said selection switch. This way, parameters associated with a sub-activity defined under the activity to be tracked can also be recorded. For example, a breastfeeding or milk-pumping mother can record from which breast the milk drain is.

In yet another embodiment of the invention, said selection switch is of type slide.

In another embodiment of the invention, said input means are tactile buttons.

In another possible embodiment of the invention, said tracking device consists of a screen associated with the said processor unit to provide the user with data related to the activity records.

In yet another embodiment of the invention, said processor unit is configured to display the record of the lastly logged activity on the user interface.

In another possible embodiment of the invention, said tracking device consists of a communication unit associated with the said processor unit to enable the recorded activities to be transmitted to an external device. This way, activity records can be transferred to other devices such as mobile phones and servers. In the case of any connection problems, activity records can be stored in the internal memory unit to prevent data loss.

In another possible embodiment of the invention, said input unit consists of a power connector to get energized, and the said tracking device consists of a power terminal for attaching/detaching the power connector.

In yet another embodiment of the invention, said power connectors are provided in the form of pogo-pins, and the said power terminals are provided in a structure compatible with those pogo-pins.

In another possible embodiment of the invention, said input unit is composed of a flexible top cover paving over the said input means to allow the users' touch to be transferred to those input means. This way, the interaction area of the said input means can be widened, allowing users with certain diseases like Parkinson to interact with the tracking device in a facilitated way.

In another possible embodiment of the invention, said tracking device consists of a liaison component to attach the tracking device to a surface or to the user. This way, the tracking devices can be used in the vicinity of the place where the activity happens.

In yet another embodiment of the invention, said liaison component can be a wearable.

In yet another embodiment of the invention, said liaison component is at least one of the wristband, necklace, magnetic material or adhesive material.

In another possible embodiment of the invention, said tracking device consists of at least one of an audio output unit or a vibration unit associated with the said processor unit; and this said processor unit is configured to trigger at least one of the said audio output or vibration units for scheduled activities. This way, users get notified when it is time for a previously planned activity.

The invention discloses an activity tracking system comprising a plurality of activity tracking devices, each having a processor unit for receiving an input signal related to an activity and a memory unit for recording at least one data associated with the said activity by the said processor unit in respect with the said input signal. In this regard, the innovation involves at least one tracking device configured to generate an activity record of at least one activity when it receives an input signal, and at least one other tracking device configured to generate an activity record of another activity which is different from the first one mentioned above.

In another possible embodiment of the invention, said activity tracking system consists of an external device for sending commands to the tracking devices and/or for receiving data from the tracking devices.

BRIEF DESCRIPTION OF THE DRAWINGS

FIGS. 8A, 8B, and 8C are the representative views of different types of input units of FIG. 2, according to an embodiment of the present disclosure.

REFERENCE NUMBERS

Figure 1:
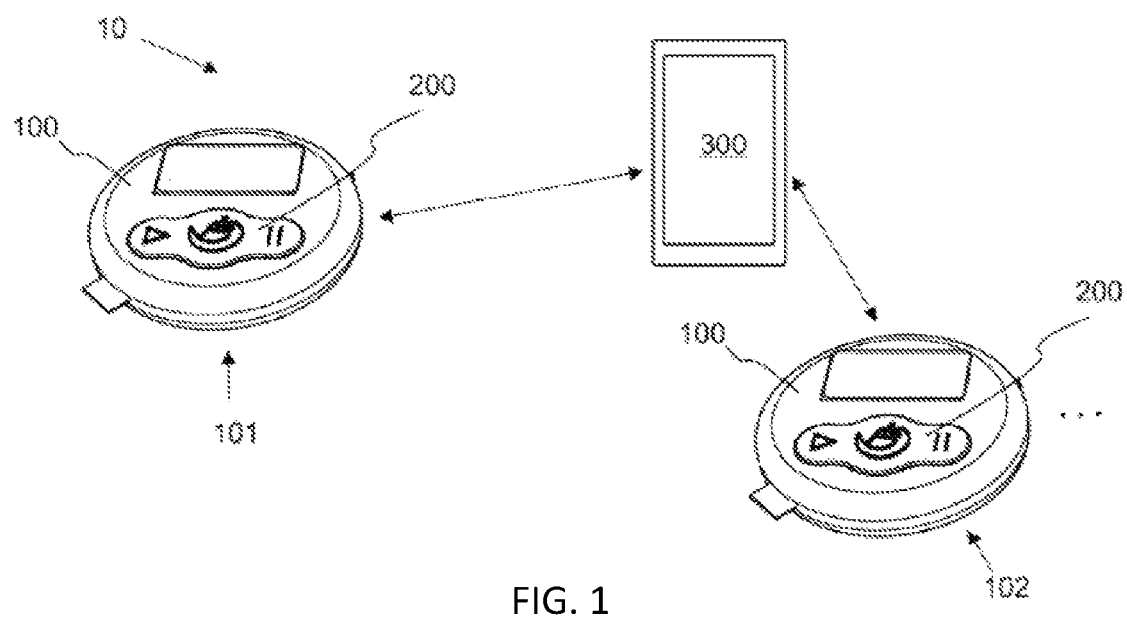
FIG. 1 is a representative view of the activity tracking system for the present disclosure.
Figure 2:
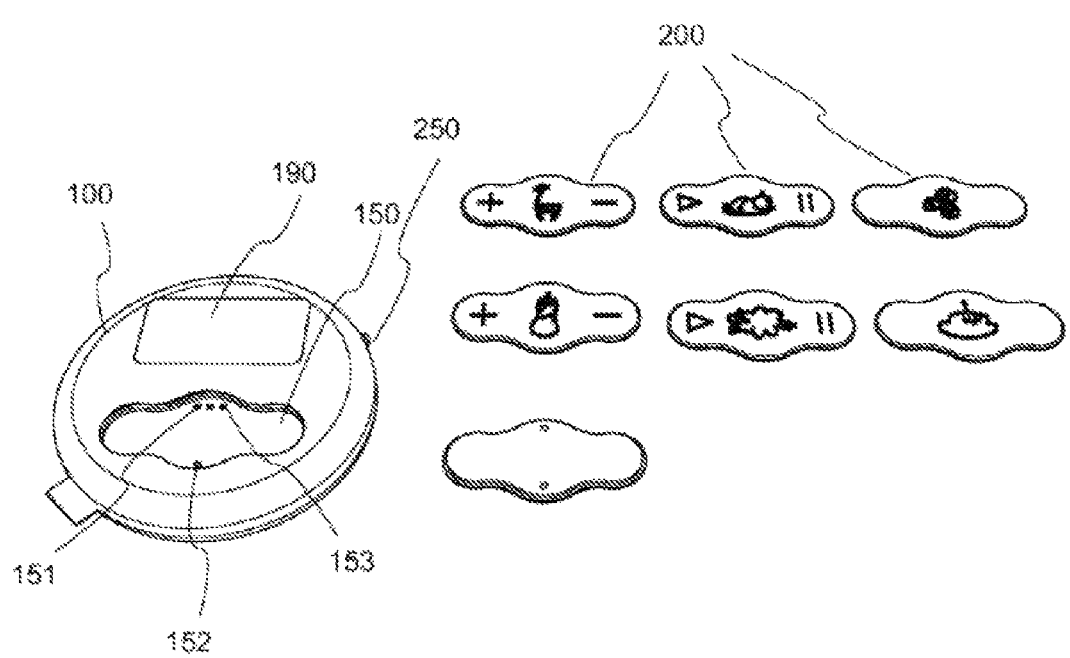
FIG. 2 is a representative view of the tracking device and the attachable/detachable input units of FIG. 1, according to an embodiment of the present disclosure.

10 Activity tracking system
100 Tracking device
101 First tracking device
102 Second tracking device
110 Processor unit
120 Memory unit
130 Communication unit
140 Body
150 Input unit slot
151 Input terminal
152 Identifier terminal
153 Power terminal
160 Primary magnetic immobilization component
190 Screen
200 Input unit
210 Input means
211 Primary input means
212 Sub-input means
220 Inlet connector
230 Identifier circuit
240 Identification component
250 Selection switch
260 Top cover
270 Power connector
280 Secondary magnetic immobilization component
300 External device

DETAILED DESCRIPTION OF THE EMBODIMENTS

In this detailed description, the invention is further explained in detail for a better understanding of the concept, with references to examples that do not expose any restrictive effect on the disclosure.

With reference to FIG. 1, the invention is essentially an activity tracking system (10) that comprises a plurality of activity tracking devices (100), each of which is specifically programmed to record a different activity, and each having an appropriate input unit (200) associated with that activity attached to its body (140). The activity tracking system (10) can consist of a first tracking device (101) that generates a record for an activity when it receives an input signal, and a second tracking device (102) that generates a record for another activity. The invention also discloses a tracking device (100), which is used in the said activity tracking system (10), that has different attachable/detachable input units (200) for different activity types. The tracking device (100) recognizes the inserted input unit (200), evaluates the input signals received from that input unit (200) according to the recognized type of the input unit (200), and records accordingly.

The aforementioned activity tracking can be exemplified for babies and newborns as breastfeeding duration, vitamin/medication intake time, urination/defecation time, crying duration, the time when the baby is happy, sleeping duration, weight, the amount of pumped milk and the breast from which the milk is pumped, bath time, amount of the medication taken, tooth-brushing time, amount of consumed food, storytelling duration, cleaning time, TV watching duration, amount of consumed water, etc. As another set of examples, activity tracking for a pet can include walking time, feeding time, or amount of consumed food; for construction equipment, it can be the maintenance time or operating time; for hotels, it can be sheet changing time, toilet cleaning time, or room ventilation time/duration, etc. All these activities require different types of user inputs. Tracking such activities include recording the activity time together with an amount associated with that activity and/or a duration associated with that activity, when relevant.

The present invention provides the user with the ability to change the input unit attached to the body of the tracking device with another input unit when desired, which enables a new type of activity to be tracked. This opportunity is available in virtue of the replaceability of the input unit.

The activity tracking system (10) comprises a plurality of tracking devices (100) and an external device (300) that exchanges activity record data with the tracking devices (100).

Figure 3:
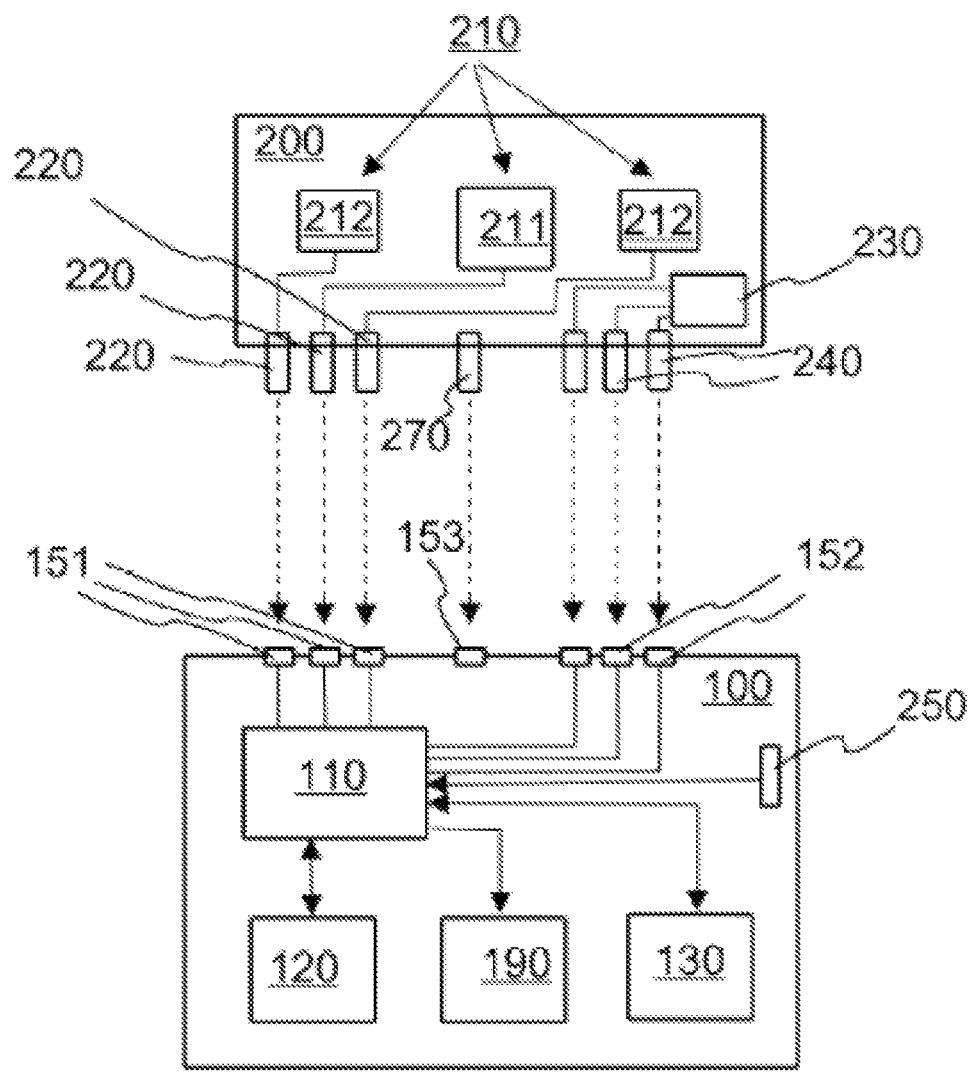
FIG. 3 is a schematic diagram of the activity tracking device of FIG. 1, according to an embodiment of the present disclosure.
Figure 4:
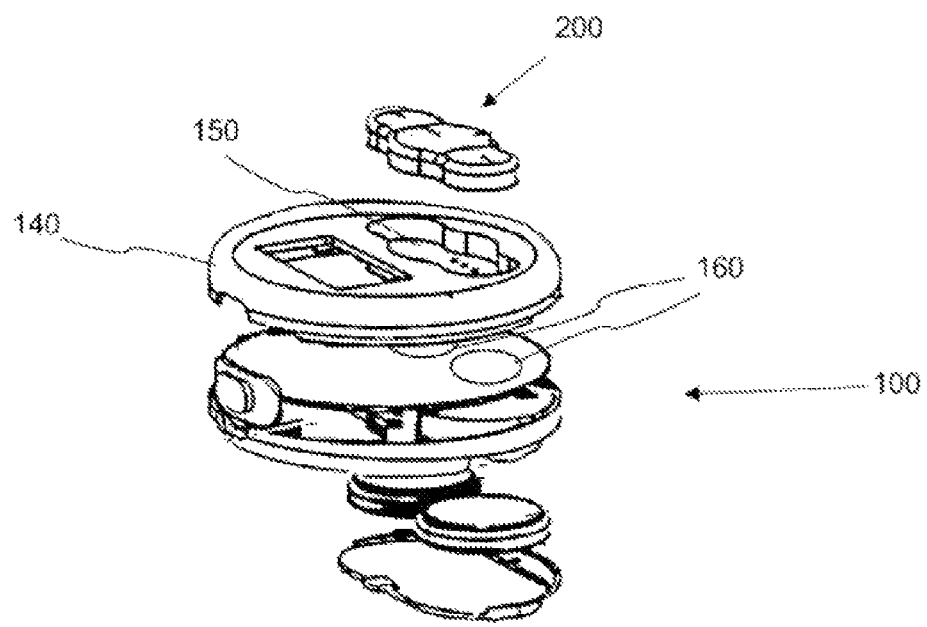
FIG. 4 is the exploded view of the activity tracking device of FIG. 2, according to an embodiment of the present disclosure.
Figure 5:
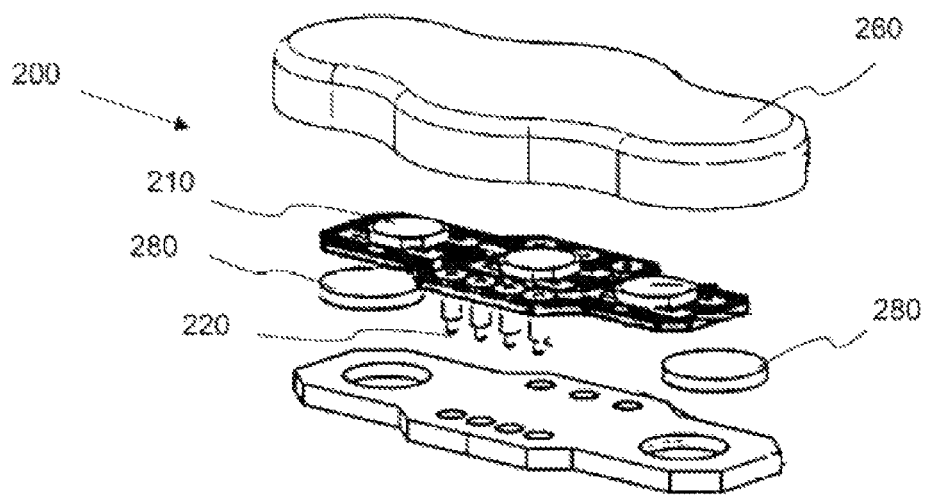
FIG. 5 is the exploded view of the input units of FIG. 2, according to an embodiment of the present disclosure.
Figure 6:
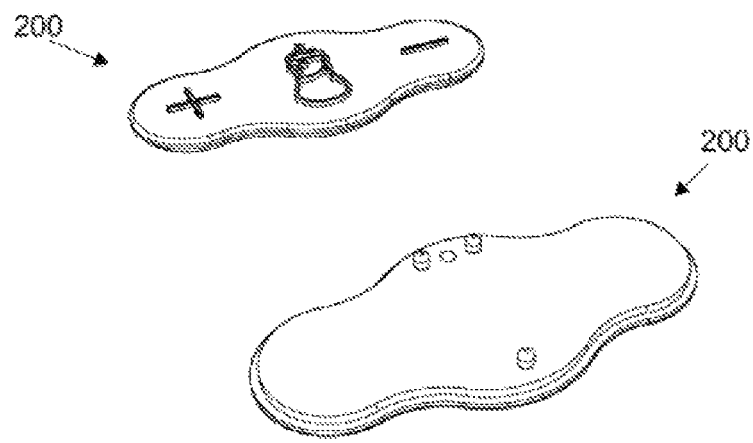
FIG. 6 includes perspective views of the input unit of FIG. 2, according to an embodiment of the present disclosure.
Figure 7:
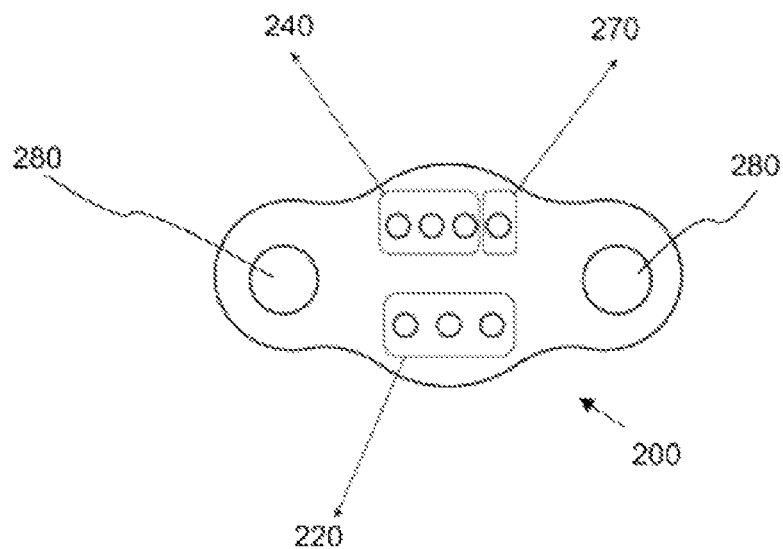
FIG. 7 is a representative view of the input unit of FIG. 2, according to an embodiment of the present disclosure.
Figure 9:
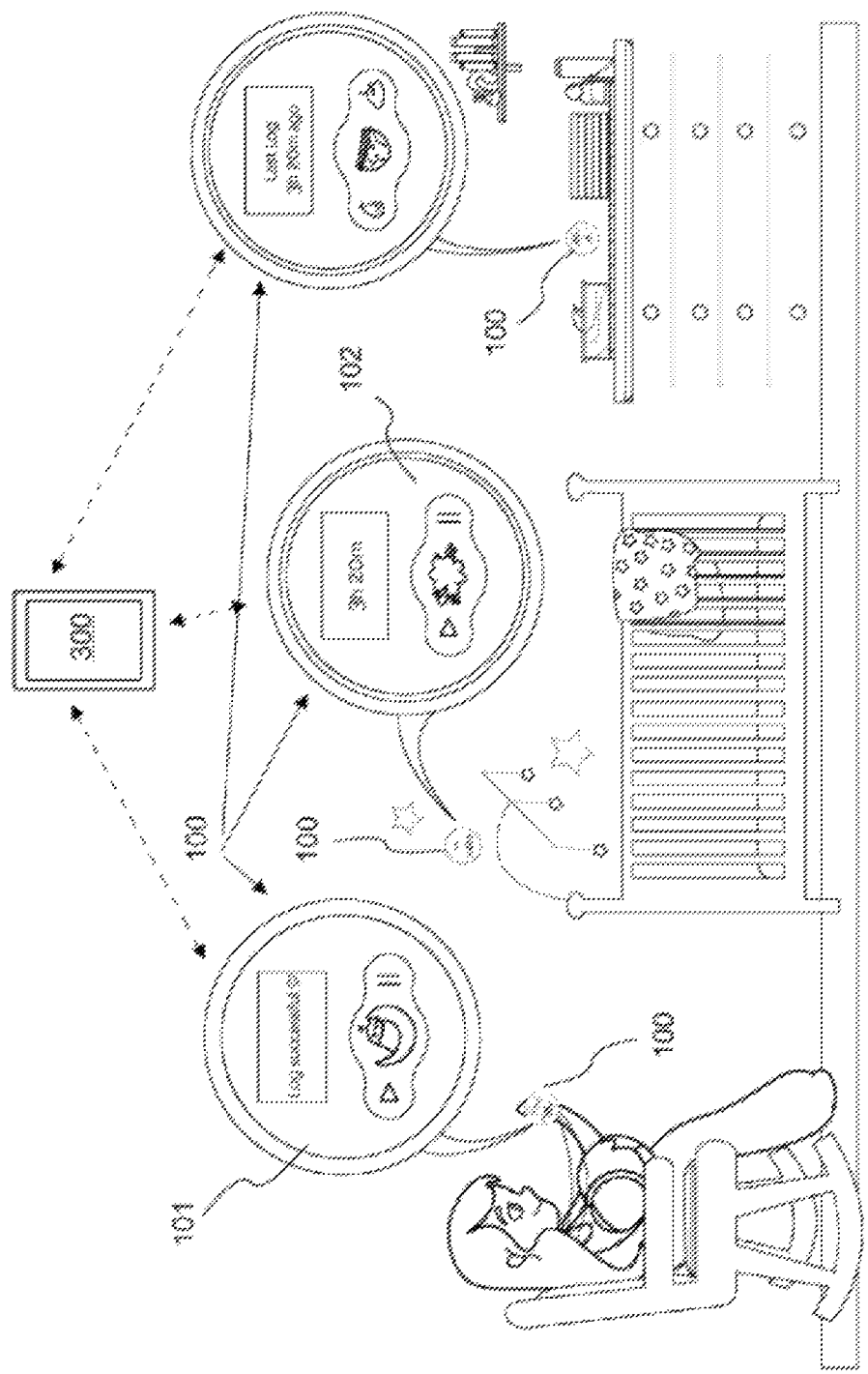
FIG. 9 is a perspective view of the disclosed activity tracking system during an in-use condition with different types of tracking devices, according to an embodiment of the disclosure.

With reference to FIG. 3 and FIG. 4, the activity tracking device (100) contains a processor unit (110) that performs predetermined process steps and/or records an activity based on the received input signal(s). The activity tracking device (100) also contains a memory unit (120) in which the processor unit (110) records data. The processor unit (110) can be a microprocessor, and the memory unit (120) may contain a temporary or permanent data storage component, or a combination thereof. The activity tracking device (100) comprises a device body (140). On the body (140) of the tracking device (100), there exists at least one input terminal associated with the processor unit (110) to transmit the said input signal to that processor unit (110). There also exists an identifier terminal (152) associated with the processor unit (110). This identifier terminal (152) supplies the electrical connection to enable the processor unit (110) to recognize the input unit (200) attached to the tracking device (100). The tracking device (100) also contains a power terminal (153) to energize the input unit (200) attached to the tracking device (100).

The input unit (200) comprises at least one input means (210) that enables an input signal to be generated when the user interacts. Each one of the input means is associated with an inlet connector (220). These inlet connectors (220) are inserted into the corresponding input terminals (151) and they provide the input signal to be transmitted to the processor unit (110). The input means (210) can be provided as tactile buttons. When the input unit (200) is attached to the tracking device (100), the inlet connectors (220) are aligned and united with the input terminal (151). When the user interacts with the tracking device (100) via the input means (210), i.e. when (s)he presses the button, the input signal will be transmitted from the input unit (200) to the processor unit (110) through a switching mechanism.

The input unit (200) comprises an identifier circuit (230), which is configured to be wiredly/wirelessly associated with the processor unit (110). The identifier circuit (230) is associated with at least one identification component (240). When the input unit (200) is attached to the tracking device (100), the identification component (240) is aligned and united with the identifier terminal (152) and establishes an electrical connection with the said processor unit (110). The identifier circuits (230) are different for the input units (200) which are assigned with different functionalities. The identifier circuits (230) that are assigned to different types of input units (200) may contain specific combinations of specific circuit components or they may generate signals with different amplitudes. The processor unit (110) determines the type of the input unit (200) attached to the tracking device (100) based on the information received from the identifier circuit (230) once the processor unit (110) establishes a connection with the identifier circuit (230). The input unit (200) can have the functionality of recording an activity, together with an amount, and/or a duration when relevant, and different input units may contain different numbers of input means (210).

In a possible embodiment of the invention, the identifier circuit can be NFC or RFID tag.

Memory unit (120) may store the types of the input units (200) and the identifier circuits matching them, and the processor unit (100) determines the type of the attached input unit (200) based on the information received from the identifier circuit (230) once connected. Thereafter, the processor unit (110) evaluates the signals received from the input means (210) based on the detected type and performs the process steps according to this type.

The said input means (210) can be primary input means (211) or sub-input means (212).

When the processor unit (110) receives the input signal from a primary input means (211), it records the activity together with the time when the input signal is received, and by associating the activity with the detected type. Such an activity record can be provided by an event-tracker typed input unit (200), which tracks only the time at which the activity happens. Each different type of an input unit (200) comprises a primary input means (211). A relevant activity record can be, for example, "Activity: Bathing, time: 19:10".

When the processor unit (110) receives the input signal from a sub-input means (212), it can perform an increment/decrement operation on an amount value in association with the detected activity. Such an activity record can be provided by an amount-tracker typed input unit (200). When the user interacts with the primary input means (211) after performing an increase/decrease operation via the sub-input means (212), i.e., pressing the relevant button until the desired amount value is reached, the final amount data is recorded together with other information related to the activity. For example, considering the milk pumping activity, the amount of the pumped milk can be provided as input to the tracking device (100) through an interaction with the sub-input means (212), by pressing the increment/decrement button(s) as required, and then when interacted with the primary input means, the amount of milk pumped will be recorded in association with the milk pumping activity. The time when this activity happens is also recorded. A relevant activity record can be, for example, "Activity: Pumping milk, Amount: 0.4 mL, time: 1:30 PM".

The processor unit (110) can start/stop a timer when it receives the input signal from the sub-input means (212). Afterwards, if it receives another input signal from a primary input means (211), then the time elapsed during these processes will be recorded together with the other information related to the activity. For example, the duration of a breastfeeding session can be recorded for a breastfeeding activity. Herein, the user presses a sub-input means (212) to start a stopwatch when she starts breastfeeding, she presses another sub-input means (212) to stop the stopwatch when breastfeeding is finished, and she presses the primary input means (211) to record the duration obtained from the stopwatch into the memory unit (120). A relevant activity record can be, for example, "Activity: Breastfeeding, Duration: 16 minutes, time: 2:36 AM".

The time tracking mentioned above can also be achieved by the process steps of recording the time at which the input signal is received from a sub-input means (212), recording another time at which the input signal is received from another sub-input means (212), and determining the difference between these two times.

FIG. 8A illustrates the input units (200) that can be used for amount tracking purposes. The sub-input means (212) with the + symbol increases the amount associated with the activity, while the sub-input means (212) with the − symbol decreases that amount, and the symbol in the middle is for the primary input means (211). That symbol can be an illustration of the activity that is associated with the input unit type.

FIG. 8A illustrates the input units (200) that can be used for time tracking purposes. The play symbol starts the stopwatch, while the pause symbol stops the stopwatch. The primary input means (211), which has an illustration expressing the activity in use, records the activity together with the determined duration.

In a possible embodiment of the invention, the tracking device (100) or the input unit (200) may comprise a selection switch (250). This selection switch (250) is associated with the processor unit (110), either via the input unit (200), which is attachable/detachable to the tracking device (100), or it can directly be on the body (140) of the tracking device (100). The processor unit (110) selects a sub-activity type related to the main activity based on the position of the selection switch (250). The selection switch (250) may optionally operate on two different positions, and is of type slide. For example, in the case of milk pumping, the processor unit (110) can record an amount value for the left breast when the selection switch (250) is in position 1, and it can record another amount value for the right breast when the selection switch (250) is in position 2. A relevant activity record can be, for example, "Activity: Milk pumping, Sub-activity: Left breast, Amount: 0.2 mL, time: 13:25".

The tracking device (100) may also comprise a screen (190) on its body (140), which is associated with the processor unit (110). The processor unit (110) enables the information regarding the last recorded activity to be displayed on the said screen (190). For example, upon the first attempt of an interaction with the tracking device (100) via the primary input means (211), the screen can present the information regarding the last recorded activity. The processor unit (110) can also trigger the screen (190) to display the type of the activity in consideration or the type of input unit (200) attached to the tracking device (100). The processor unit (110) can further trigger the screen (190) to display information regarding the amount and/or duration associated with the activity in use, or the recorded/present time at which the activity happened. The tracking device (100) may also contain an on/off switch (not shown in the figures) on its body (140).

The tracking device (100) comprises an input unit slot (150) for inserting the input unit (200). Said input unit slot (150) has a form compatible with the said input unit (200), and houses the connection terminals at its base. The input unit (200) is positioned in a way that is compatible with the input unit slot (150), and when inserted, the connection components are aligned and united with the connection terminals.

The connection components are provided by pogo-pins.

The tracking device (100) comprises at least one primary magnetic immobilization component (160) and the input unit (200) comprises at least one secondary magnetic immobilization component (280). These magnetic immobilization components (160 and 280) are made of materials such that at least one of them attracts the other by applying magnetic force. One of the primary and secondary magnetic immobilization components (160 and 280) can be a magnet, and the other one can be a magnet or a ferromagnetic material. The primary magnetic immobilization component (160) is provided in the vicinity of the base of the input unit slot (150), and the secondary magnetic immobilization component (280) is provided in the vicinity of the side of the input unit (200) which connects to the base of the input unit slot (150).

In a possible embodiment of the invention, the tracking device can have two for each primary and secondary magnetic immobilization components (160 and 280).

The input unit (200) comprises a top cover (260) paving over the input means (210). This top cover (260) is made of a material which is flexible enough to allow the user to interact with the input means (210) when the top cover (260) is pressed. Said top cover (260) also comprises cartouches (embossment symbols), which allows visually impaired people to interact with the tracking device (100) in a facilitated manner through the input unit (200).

The tracking device (100) comprises a communication unit (130) that is associated with the processor unit (110). This communication unit (130) provides the activity records to be transmitted to an external device (300). The communication unit (130) communicates wirelessly by means of radio waves. Therefore, it can be, for example, a Wi-Fi module or a Bluetooth module. On the other hand, said external device (300) can be a server, a computer, or a mobile device coupled with the tracking device (100). In the case of the external device (300) being a mobile phone or a computer, an application can be installed on that external device such that it can display the data received from the tracking device (100) or it can send commands to program the tracking device (100).

The tracking device (100) may comprise at least one of a vibration unit and an audio output unit controlled by the processor unit (110). The processor unit (110) can then trigger the operation of either the vibration unit or the audio output unit or both for scheduled activities that are stored in the memory unit (120). Said scheduled activity time can be adjusted by the input means (210).

The tracking device (100) may comprise a liaison component. This component enables the tracking device (100) to be attached to a surface or to the user. The liaison component can be a wearable like a wristband, a necklace chain, etc.; it can also be a magnet so that the tracking device (100) can be used on surfaces like refrigerators; or it may contain an adhesive material so that the tracking device (100) can be used on walls. In a preferred embodiment of the invention, the liaison component is a tag through which a product like necklace chain can be passed.

The tracking device (100) may comprise a power source, which can be a battery.

The processor unit (110) can also be programmed by an external device (300) through the communication unit (130). The external device (300) may determine the activity type, an account to which the recorded activities will be associated, or the times of the scheduled activities.

The protection scope of the present invention is set forth in the annexed claims and cannot be restricted to the illustrative disclosures or the exemplary descriptions of the invention embodiments given above, under the detailed description. Yet a person skilled in the relevant art can obviously produce similar embodiments and achieve substantially equivalent results under the light of the foregoing disclosures, without departing from the main principles of the present invention.

I claim:

1. A tracking device, comprising a processor unit for receiving an input signal related to an activity, and a memory unit for enabling the processor unit to perform at least one activity recording related to the activity and in relation to the input signal, wherein:

the tracking device further comprises at least one input unit configured to be detachably attached onto a device body, and at least one input terminal associated with the processor unit within the device body to enable the input signal to be transmitted to the processor unit;

the at least one input unit is configured for a user to interact with the tracking device to generate the input signal, an inlet connector detachably attached to the at least one input terminal to enable the input signal generated by the at least one input unit to be transmitted to the processor unit, and an identifier circuit enabling the processor unit to determine a type of the at least one input unit when the identifier circuit is linked to the processor unit; and the processor unit is configured to detect the type of the at least one input unit via the identifier circuit when the processor unit is linked to the identifier circuit, and to evaluate the input signal received from the at least one input unit in accordance with the type of the at least one input unit detected, wherein the at least one input unit comprises a primary input means and a sub-input means, and in response to the processor unit receiving the input signal from the primary input means, the processor unit is further configured to:

perform process steps matching the type of the at least one input unit detected in the case of receiving an input signal from one of the sub-input means; and generate an activity record for the activity matching the type of the at least one input unit detected based on a result of the process steps of the activity, wherein the process steps are at least one of the following:

incrementing an amount associated with the activity by a predetermined value, or decrementing the amount associated with the activity by the predetermined value.

2. The tracking device of claim 1, wherein:
the processor unit comprises at least one identifier terminal associated with the processor unit to enable the processor unit to detect the type of the at least one input unit attached to a body of the tracking device; and
the at least one input unit comprises at least one identification component, wherein the at least one identification component is associated with the identifier circuit and configured to be connected with the at least one identifier terminal in an attachable and detachable manner to enable the identifier circuit to be connected to the processor unit.

3. The tracking device of claim 1, wherein the processor unit is further configured to generate an activity record for the activity matching the type of the at least one input unit detected when the processor unit receives the input signal.

4. The tracking device of claim 1, wherein the process further comprises:
recording a time when the input signal is received from a first one of the sub-input means as a first time,
recording a time when the input signal is received from a second one of the sub-input means as a second time, and
determining a difference between the second time and the first time.

5. The tracking device of claim 1, wherein the process further comprises:
starting a stopwatch when the input signal is received from a first one of the sub-input means,
stopping the stopwatch when the input signal is received from a second one of the sub-input means, and
determining an elapsed time.

6. The tracking device of claim 1, wherein the tracking device further comprises an input unit slot, wherein the input unit slot has a form compatible with a form of the at least one input unit to enable an insertion of the at least one input unit.

7. The tracking device of claim 6,
wherein the tracking device further comprises a primary magnetic immobilization component, and the at least one input unit comprises a secondary magnetic immobilization component, and
wherein one of the primary magnetic immobilization component and the secondary magnetic immobilization component is a magnet, and an other one of the primary magnetic immobilization component and the secondary magnetic immobilization component is either the magnet or a ferromagnetic material.

8. The tracking device of claim 1, wherein the at least one input unit or the tracking device comprises a selection switch operating in two different positions; and
the processor unit is further configured to perform the process steps and to record the activity in respect with a position of the selection switch.

9. The tracking device of claim 8, wherein the selection switch is a sliding switch.

10. The tracking device of claim 1, wherein the at least one input unit is a tactile button.

11. The tracking device of claim 1, wherein the tracking device further comprises a screen associated with the processor unit.

12. The tracking device of claim 11, wherein the processor unit is further configured to display a record of a lastly logged activity on a user interface.

13. The tracking device of claim 1, wherein the tracking device further comprises a communication unit associated with the processor unit to enable the activity recorded to be transmitted to an external device.

14. The tracking device of claim 1, wherein the at least one input unit further comprises a power connector to get energized, and
the tracking device further comprises a power terminal for attaching or detaching the power connector.

15. The tracking device of claim 14, wherein the power connector is provided in a form of a pogo-pin, and the power terminal is provided in a structure compatible with the pogo-pin.

16. The tracking device of claim 1, wherein a flexible top cover paves over the at least one input unit to allow a touch of the user to be transferred to the at least one input unit.

17. The tracking device of claim 1, wherein the tracking device further comprises a liaison component to attach the tracking device to a surface or to the user.

18. The tracking device of claim 17, wherein the liaison component is a wearable.

19. The tracking device of claim 17, wherein the liaison component is at least one selected from the group consisting of a wristband, a necklace, a magnetic material, and an adhesive material.

20. The tracking device of claim 1, wherein the tracking device further comprises at least one of an audio output unit or a vibration unit associated with the processor unit; and
the processor unit is further configured to trigger the at least one of the audio output unit and the vibration unit for scheduled activities.

21. An activity tracking system, comprising a plurality of activity tracking devices, each of the plurality of activity tracking devices is a tracking device having a processor unit for receiving an input signal related to an activity and a memory unit for enabling the processor unit to perform at least one activity recording related to the activity according to the input signal,
wherein among the plurality of activity tracking devices, the activity tracking system comprises a first tracking device and a second tracking device, wherein the first tracking device is configured to generate a first activity record related to a first activity when the first tracking device receives the input signal, and the second tracking device is configured to generate a second activity record related to a second activity, wherein the first activity and the second activity are different from each other,
wherein the tracking device further comprises at least one input unit configured to be detachably attached onto a device body;
wherein the at least one input unit comprises a primary input unit and a sub-input unit, and
in response to the processor unit receiving the input signal from the primary input unit, the processor unit is further configured to:
perform process steps matching a type of the at least one input unit detected in the case of receiving an input signal from one of the sub-input unit; and
generate an activity record for the activity matching the type of the at least one input unit detected based on a result of the process steps of the activity,
wherein the process steps are at least one of the following:
incrementing an amount associated with the activity by a predetermined value, or
decrementing the amount associated with the activity by the predetermined value.

22. The activity tracking system of claim 21, wherein:
the tracking device further comprises at least one input terminal associated with the processor unit within the device body to enable the input signal to be transmitted to the processor unit;
the at least one input unit is configured for a user to interact with each of the plurality of tracking devices to generate the input signal, an inlet connector detachably attached to the at least one input terminal to enable the input signal generated by the at least one input unit to be transmitted to the processor unit, and an identifier circuit enabling the processor unit to determine a type of the at least one input unit when the identifier circuit is linked to the processor unit; and
the processor unit is configured to detect the type of the at least one input unit via the identifier circuit when the processor unit is linked to the identifier circuit, and to evaluate the input signal received from the at least one input unit in accordance with the type of the at least one input unit detected.

23. The activity tracking system of claim 21, wherein the activity tracking system comprises an external device for sending commands to the plurality of activity tracking devices and/or receiving data from the plurality of activity tracking devices.

* * * * *